US009232969B2

(12) United States Patent
Farris

(10) Patent No.: US 9,232,969 B2
(45) Date of Patent: Jan. 12, 2016

(54) DIRECTIONAL CONTROL FOR A MULTI-AXIAL SCREW ASSEMBLY

(75) Inventor: Robert A. Farris, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 447 days.

(21) Appl. No.: 12/915,634

(22) Filed: Oct. 29, 2010

(65) Prior Publication Data

US 2012/0109218 A1 May 3, 2012

(51) Int. Cl.
*A61B 17/70* (2006.01)

(52) U.S. Cl.
CPC ......... *A61B 17/7038* (2013.01); *A61B 17/7037* (2013.01)

(58) Field of Classification Search
CPC .................. A61B 17/7037; A61B 17/7038
USPC ......... 606/301–308, 319, 328, 246, 264–272, 606/277, 278, 324, 325
See application file for complete search history.

(56) References Cited

U.S. PATENT DOCUMENTS

| | | | |
|---|---|---|---|
| 5,443,467 A * | 8/1995 | Biedermann et al. ........... 606/65 |
| 5,733,285 A * | 3/1998 | Errico et al. .................. 606/278 |
| 5,882,350 A * | 3/1999 | Ralph et al. ................... 606/278 |
| 2004/0097933 A1* | 5/2004 | Lourdel et al. .................. 606/61 |
| 2005/0154391 A1* | 7/2005 | Doherty et al. ................. 606/61 |
| 2008/0132959 A1* | 6/2008 | Mikkonen et al. ............ 606/308 |
| 2010/0152787 A1* | 6/2010 | Walsh et al. .................. 606/308 |
| 2010/0204735 A1* | 8/2010 | Gephart et al. ............... 606/264 |
| 2010/0305621 A1* | 12/2010 | Wang et al. .................... 606/305 |
| 2011/0112578 A1* | 5/2011 | Keiser et al. .................... 606/264 |
| 2011/0160779 A1* | 6/2011 | Schlaepfer ......... A61B 17/7035 606/305 |
| 2011/0178558 A1* | 7/2011 | Barry ............................ 606/302 |

* cited by examiner

*Primary Examiner* — Jan Christopher Merene
*Assistant Examiner* — Atiya Mahmud
(74) *Attorney, Agent, or Firm* — Sorell Lenna & Schmidt LLP

(57) ABSTRACT

A multi-axial screw assembly comprises a receiver, a base member, and a crown. The receiver comprises a channel for receiving a rod and an aperture extending from a bottom portion of the receiver. The base member comprises an aperture extending through the base member and an opening on a bottom portion of the base member. The base member is configured to couple to the receiver such that the aperture of the receiver is generally aligned with the aperture of the base member. The base member is rotatable relative to the receiver. The crown is received in the receiver and configured to mate to the base member. The crown has a mating feature configured to couple to the base member such that the crown rotates the base member when the crown is rotated.

14 Claims, 4 Drawing Sheets

DIRECTIONAL CONTROL FOR A MULTI-AXIAL SCREW ASSEMBLY

FIELD OF INVENTION

Embodiments of the invention relate to implants used for correction of orthopedic injuries or deformities, and more specifically, but not exclusively, relate to multi-axial screws implanted in bone for stabilizing longitudinal support members.

BACKGROUND

Typical implant systems include several pieces, which may be associated or useful with only specific other pieces. Among such pieces are screws, hooks rods, plates and similar longitudinal members for supporting, holding and/or correcting one or more bones. Such longitudinal members can be fastened to bones via direct or indirect connection to hooks, screws, bolts or other fasteners, and may be linked to each other by a variety of connectors. In the spinal field, for example, screws or other fasteners can be attached to two or more vertebrae, the vertebrae can be adjusted into their normal or a therapeutically better position, and longitudinal members are connected to the fasteners so that the vertebrae are held in the normal or therapeutically improved position.

Accordingly, known bone screws, hooks, clamps and other bone fasteners or fixation devices can be connected or adjoined to a particular bone or bones as a connection between the remainder of the implant and the bone(s). Where a rod is used as a support and stabilizing member, commonly a series of two or more screws are inserted into two or more vertebrae to be instrumented. A rod is then placed within or coupled to the heads of the screws, or is placed within a connecting device that links the rod and a screw head, and the connections are tightened. In this way, a rigid supporting structure is fixed to the vertebrae, with the rod providing the support that maintains and/or promotes correction of the vertebral malformation or injury.

Some devices allow one or more degrees of freedom between a fastening portion or fastening member and a receiving portion or member, reducing the required precision of placement of the fixation device, since a head portion of the fixation device is multi-axially positionable around the bone-threaded or hook portion. The head can thus be positioned so as to easily receive the rod, limiting or removing much of the positioning difficulty inherent in prior devices. However, such devices provide a single maximum angle between the fastening portion and the receiving portion for every relative orientation of those parts. Other devices have made possible a larger maximum angle between the fastening portion and the receiving portion when the fastening portion occupies one position with respect to the receiving portion, but allow only a smaller maximum angle when the fastening portion occupies any other position with respect to the fastening portion.

The description herein of problems and disadvantages of known apparatuses, methods, and devices is not intended to limit the invention to the exclusion of these known entities. Indeed, embodiments of the invention may include, as a part of the embodiment, portions or all of one or more of the known apparatus, methods, and devices without suffering from the disadvantages and problems noted herein.

SUMMARY OF THE INVENTION

An embodiment of the invention may include a multi-axial screw assembly comprising a receiver, a base member, and a crown. The receiver comprises a channel for receiving a rod and an aperture extending from a bottom portion of the receiver. The base member comprises an aperture extending through the base member and an opening on a bottom portion of the base member. The base member is configured to couple to the receiver such that the aperture of the receiver is generally aligned with the aperture of the base member. The base member is rotatable relative to the receiver. The crown is received in the receiver and configured to mate to the base member. The crown has a mating feature configured to couple to the base member such that the crown rotates the base member when the crown is rotated.

Yet another embodiment may include a method of implanting a multi-axial screw in bone. A step includes installing a bone screw member of the multi-axial screw in bone. Another step includes rotating a crown located within a receiver attached to the bone screw member, thereby rotating a base member relative to the receiver. The method locates a preferred position of the base member relative to the receiver. The preferred position is located such that a portion of the base member allows for greater angulation at the preferred position than at other positions rotationally oriented around the base member.

Additional aspects and features of the present disclosure will be apparent from the detailed description and claims as set forth below.

DETAILED DESCRIPTION

Figure 1:
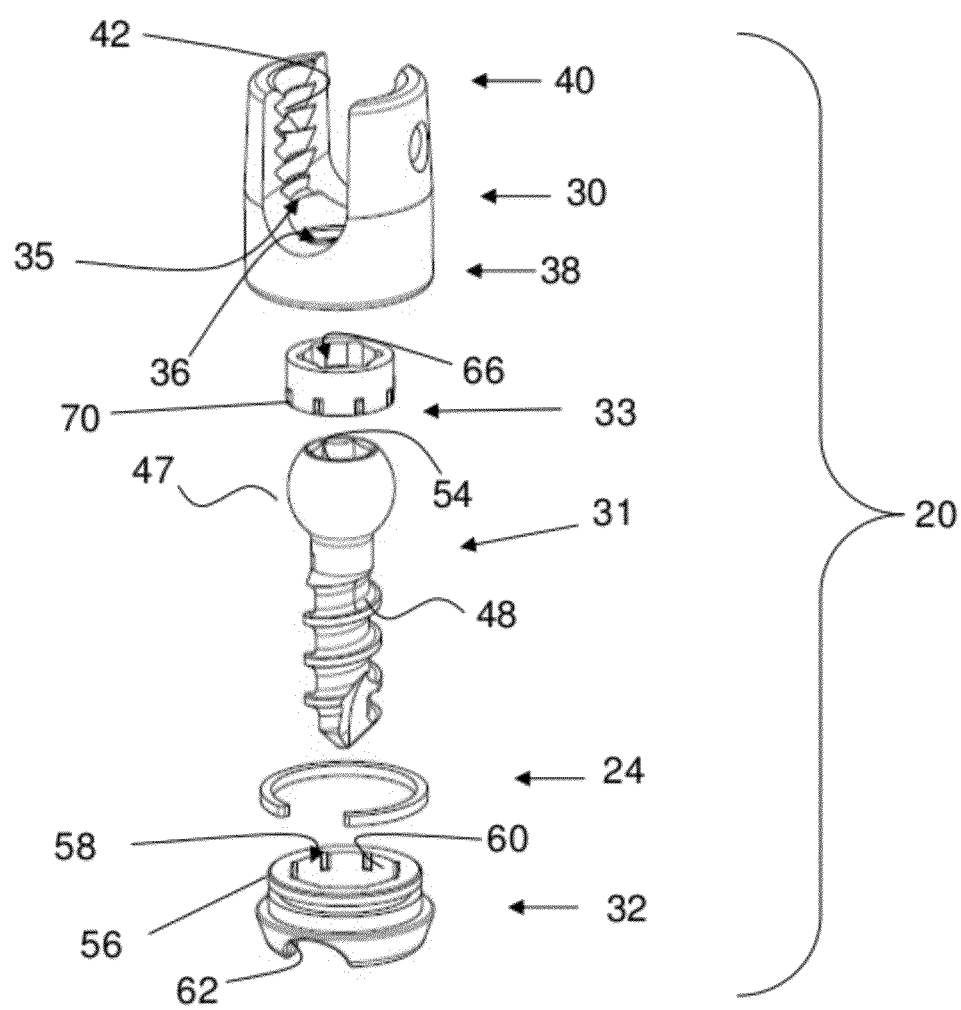
FIG. 1 is an exploded view of a multi-axial screw according to an aspect of the invention.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 is an exploded view of a multi-axial screw assembly 20 according to an aspect of the invention. Multi-axial screw assembly 20 includes a snap ring 24, a receiver member 30, a bone anchoring member 31, a base or retaining member 32, and a crown 33. Receiver member 30 has a channel 35 therethrough adapted to accommodate a rod or other longitudinal member. An aperture 36, which may be cylindrical, extends from a lower portion 38 of receiver member 30 transversely to and in communication with channel 35. In a specific embodiment, aperture 36 extends from the lower portion 38 to a top portion 40 of receiver member 30, and aperture 36 has a threaded portion 42 at or near top portion 40 for use with a compression member (for example, a set screw or other element with external threads). Threaded portion 42 could be outside of receiver member 30 if an external compression member is used. Alternatively, receiver member 30 could be externally and/or internally configured for compression members using snapping, twisting or other types of closures. The lower portion 38 of receiver member 30 has a groove 44

Figure 3:
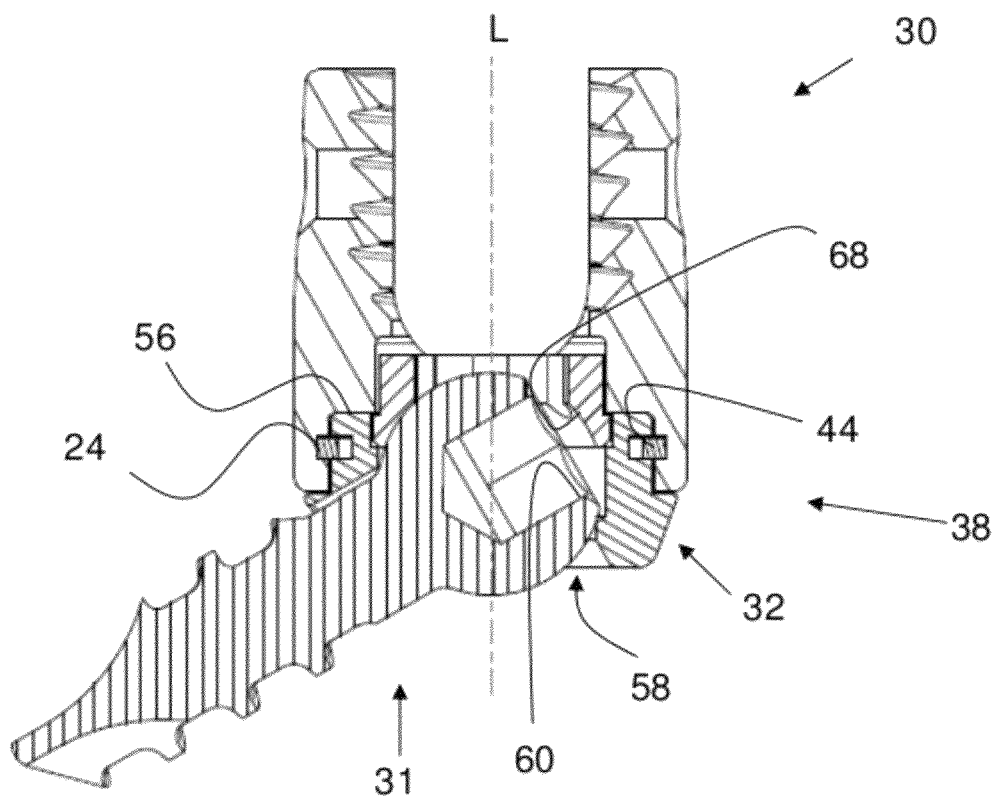
FIG. 3 is a cross section view of the embodiment of FIG. 1.

(FIG. 3). In the illustrated embodiment, groove 44 extends around the entire circumference of aperture 36.

Base or retaining member 32 in the embodiment shown in FIG. 1 is substantially circular in one embodiment with a flange 56 and a center aperture 58. Center aperture 58 is bounded by wall 60. As examples, wall 60 may be a portion of a cone or sphere, or may form a sharp edge. Base member 32 includes an opening 62 in its circumference. Aperture 58 is shown in one embodiment as substantially circular, but could also have a conical, spherical, stepped, recessed, and/or other configuration. Aperture 58 allows a head portion 47 of bone anchoring member 31 to rotate with respect to base member 32, allowing positioning of bone anchoring member 31 at any of a variety of angles with respect to longitudinal axis L of receiver member 30. Alternatively, in another embodiment the base member 32 may generally form a C-shaped element and the embodiment of the opening 62 in base member 32 would be a slot extending along the side of the base member 32. In either embodiment, a relief is made in the base 32 to allow for extra angulation into the relief.

The base member 32 can be rotated with respect to the receiver 30. This allows the opening 62 of the base member to be rotationally oriented with respect to the receiver 30. The maximum angle, then, achieved through the opening 62 of the base may be achieved at any relative orientation to the receiver 30 by rotating the base 32 relative to the receiver 30 to the proper position.

Crown 33 includes an internal aperture 66, an undersurface 68 (FIG. 3), and mating features 70. Crown 33 is sized to fit within aperture 36 of receiver member 30, so that crown 33 has some freedom of axial movement within aperture 36. Internal aperture 66 is provided to allow access to a tool receiving feature 54 in bone anchoring member 31 when crown 33 is above or atop bone anchoring member 31. Undersurface 68 is preferably configured to accommodate at least a part of head portion 47 of bone anchoring member 31. For example, undersurface 68 may be shaped (e.g. spherical, rounded, conical, or otherwise) to allow relative movement between crown 33 and part or all of head portion 47 of bone anchoring member 31. In the embodiment in which both undersurface 68 and head portion 47 have a rounded or spherical portion, undersurface 68 may have substantially the same diameter as head portion 47.

Mating features 70 of the crown 33 mate with mating base features 72 (FIG. 4) of the base 32. These features 70 and 72 are configured to mate the crown 33 to the base 32. The crown 33, then, may control the rotation of the base 32 relative to the receiver 30. This allows the base 32 to be controlled and positioned by adjusting the crown 32. The position of the base 32 may then be controlled from above the receiver 30.

Mating features 70 of the crown 33 may be projections from the side of the crown 33, or may be indentations to receive projections from the base. These features 70 may extend to a portion of the crown 33 that overlaps the base 32, or may extend between the crown 33 and the base 32.

Snap ring 24 is received between the base 32 and the receiver 30. The snap ring axially fixes the base 32 to the receiver 30 while allowing relative rotation between these parts 30 and 32. The snap ring 24 is received under the flange 56 of the base 32. The snap ring 24, when it expands, sits under the flange 56 in the groove 44 inside the receiver 30 (FIG. 3).

Figure 2:
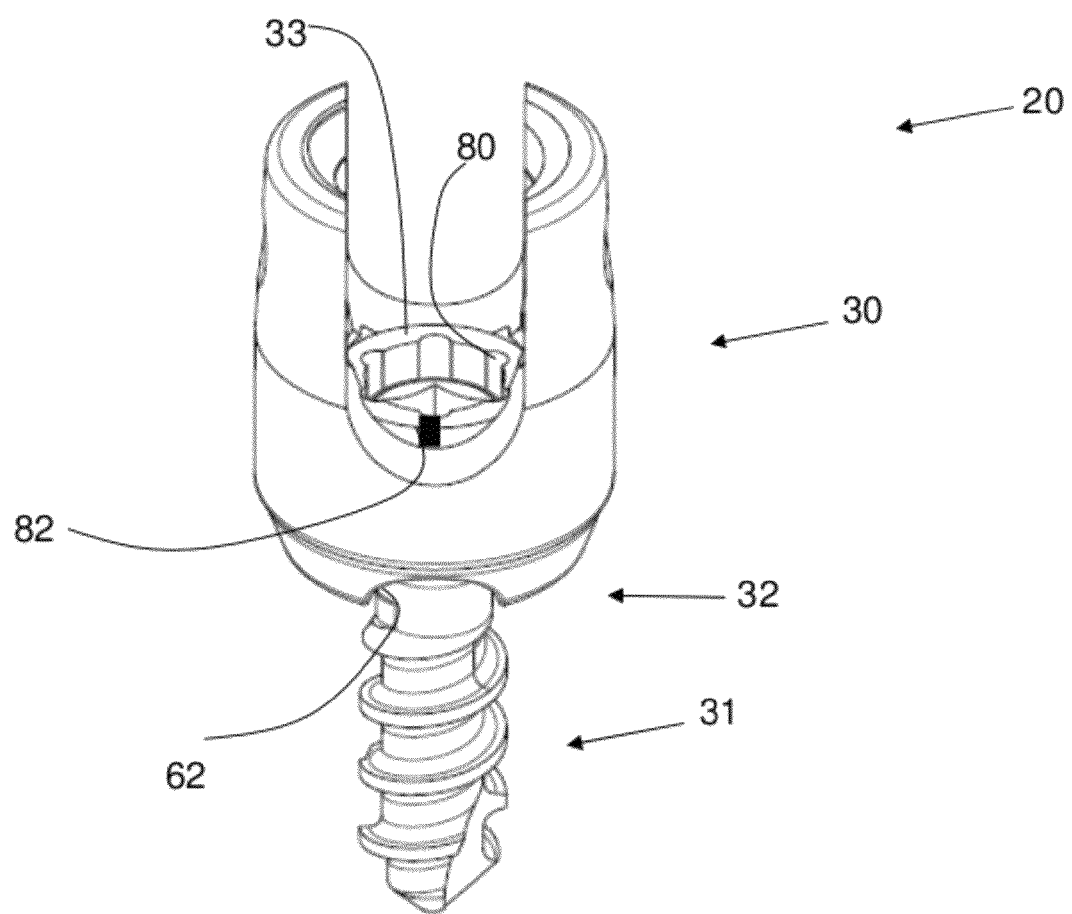
FIG. 2 is an orthogonal view of the embodiment of FIG. 1.

FIG. 2 is an orthogonal view of the embodiment of FIG. 1. The multi-axial screw assembly 20 may be assembled into a single piece prior to implantation. The receiver 30 and the base 32 capture the bone anchoring member 31. The head of the bone anchoring member 31, then, is fixed axially with respect to the receiver 30. The bone anchoring member 31 may rotate freely against the base 32, and may be oriented to angle relative to receiver 30. When this bone screw assembly 20 is implanted, a surgeon may rotate the bone screw portion 31 to secure the assembly 20 in bone, rotate the base 32 of the assembly 20 to orient the opening 62 and angle the receiver 30 relative to the bone anchoring member 31 such that the bone anchoring member 31 is received in the opening 62, and move a longitudinal member such as a rod into the receiver 30.

Internal gripping surfaces 80 of the crown 33 may engage a tool used to rotate the crown 33 thereby rotating the base 32. The surfaces 80 may be irregular in shape or evenly distributed around the internal surface of the crown 33. The crown 33 may also include a reference 82 to locate the crown 33 relative to the base 32. The reference 82 may locate the opening 62 of the base 32 relative to the receiver 30. The reference 82 may be located over the opening 62 so that a surgeon may be able to look at the assembly 20 from above and locate the base by locating the reference 82. If the surfaces 80 of the crown 33 are irregular, the irregularity may also locate the opening 62 below. For example, a surface feature of the crown 33 may receive a tool in an orientation such that the tool orientation defines the position of the opening 62.

FIG. 3 is a cross section view of the embodiment of FIG. 1. The mating features 70 and 72 between the crown 33 and the base 32 are shown. The mating features 70 and 72 are engaged when the bone screw is assembled. In this embodiment, the crown 33 is received within the base 32 so that the base 32 may be rotated relative to the receiver 30 by rotation of the crown 33.

It will be noted that the interference of base member 32 and shank portion 48 of bone anchoring member 31 determines a first maximum angle between bone anchoring member 31 and axis L for at least a portion of the relative positions of bone anchoring member 31 and base member 32. Opening 62 acts as a slot or elongation of center aperture 58, so that when bone anchoring member 31 is oriented so that shank portion 48 is substantially aligned with the opening portion 62, a second, larger maximum angle between bone anchoring member 31 and axis L is available because interference between shank 48 and base member 32 is either eliminated or moved outward. In other words, opening portion 62 provides space in which at least a part of shank portion 48 can extend to provide a greater maximum angle.

FIG. 3 also shows the snap ring 24 residing between the base 32 and the receiver 30. The snap ring 24 captures the base 32 within the receiver 30. This keeps the base 32 connected to the receiver 30 by interference between the snap ring 24 and the receiver 30 and interference between the snap ring 24 and the base 32.

The receiver 30, then, is rotatable relative to the base 32. After a surgeon has implanted the bone screw 31, the base 32 may be rotated to a position where the opening 62 is aligned with the direction of the screw 31 relative to the receiver 30. The bone screw 31 extends into the opening 62 so that the maximum angulation may be achieved. That angulation, between the bone screw and the receiver, allows for greater directional possibilities for the surgeon. The maximum angulation gives more versatility for optimal placement of the screw 31 in the bone. For example, anatomical structures may require certain angulations in order to avoid neurovascular impingement. The angulation may also aid in deformity correction by allowing additional motion between the receiver 30 and the rod during assembly. The receiver 30 may also be rotated relative to the base 32. The rotation of the receiver 30 allows for the channel 35 of the receiver 30 to be rotated into alignment along the longitudinal axis of the longitudinal member.

Figure 4:
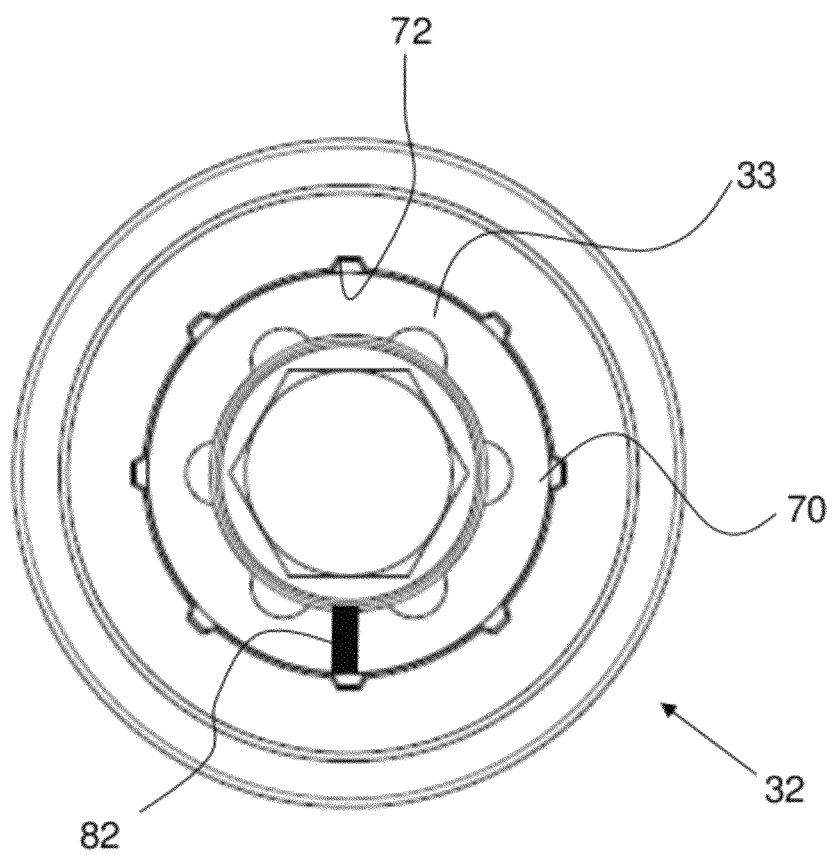
FIG. 4 is a top view of parts of the embodiment of FIG. 1.

FIG. 4 is a top view of parts of the embodiment of FIG. 1. The mating features 70 and 72 of the crown 33 and base 32 are shown from above. Additionally, the reference 82 is shown from above. As the surgeon is implanting the screw assembly 20, this view from above may be his best guide to locating the opening 62 and orienting the direction of the opening 62. The surgeon may implant a screw assembly 20 at a high relative angle between the receiver 30 and the screw 31, and be able to orient the receiver properly by rotating the crown (thereby rotating the base) so that the screw 31 sits in the opening 62 of the base 32.

The crown 33 is configured to mate to the base member 32 in order to allow rotational control through the crown 33. The mating may be an interlocking engagement such as shown in FIG. 4 where portions of the crown 33 extend radially outward from the crown and into a space in the base member 32. The interlocking engagement may be accomplished through an overlapping of portions of the crown 33 and the base member 32. Additionally, portions of the crown 33 and base 32 may be coincident. These embodiments allow for a rotational transmission of torque from the crown 33 to the base 32 in order to rotate the base 32 relative to the bone screw 31.

The foregoing detailed description is provided to describe the invention in detail, and is not intended to limit the invention. Those skilled in the art will appreciate that various modifications may be made to the invention without departing significantly from the spirit and scope thereof.

Furthermore, it is understood that all spatial references, such as "first," "second," "exterior," "interior," "superior," "inferior," "anterior," "posterior," "central," "annular," "outer," and "inner," are for illustrative purposes only and can be varied within the scope of the disclosure.

The invention claimed is:

1. A multi-axial screw assembly, comprising:
   a receiver defining a longitudinal axis and comprising a channel extending transverse to the longitudinal axis for receiving a rod and an aperture extending parallel to the longitudinal axis between a proximal portion and a distal portion;
   a base member comprising an aperture extending parallel to the longitudinal axis through a planar uppermost surface and an opposite bottom surface of the base member and an opening having a convex cutout extending from the bottom surface of the base member into a sidewall of the base member, the base member configured to couple to the receiver such that the aperture of the receiver is generally aligned with the aperture of the base member, the base member being rotatable relative to the receiver;
   a crown received in the receiver such that the crown is rotatable relative to the receiver, the crown being configured to mate to the base member, the crown having a width that is less than a width of the distal portion and greater than a width of the proximal portion, the crown having a mating feature configured to couple to the base member such that the crown rotates the base member when the crown is rotated; and
   a bone screw located between the base member and the crown such that a head of the bone screw directly engages a concave bottom surface of the crown, the bone screw being movable between a first orientation in which a shaft of the bone screw is parallel to the longitudinal axis and is spaced apart from the cutout and a second orientation in which the shaft is transverse to the longitudinal axis and at least a portion of the shaft is disposed in the cutout.

2. The multi-axial screw assembly of claim 1, wherein the mating feature includes a surface projection extending from a side wall of the crown.

3. The multi-axial screw assembly of claim 2, wherein the mating feature includes a plurality of surface projections extending from the side wall of the crown.

4. The multi-axial screw assembly of claim 2, wherein the crown further comprises an aperture, a wall of the aperture including a gripping surface configured to engage a tool such that the tool rotates the crown.

5. The multi-axial assembly of claim 4, wherein the crown further comprises a reference, the reference identifying the position of the opening of the base member.

6. The multi-axial assembly of claim 1, wherein the crown further comprises a reference, the reference identifying the position of the opening of the base member.

7. The multi-axial assembly of claim 6, wherein the reference is a tool engagement feature on the crown.

8. The multi-axial assembly of claim 1, wherein the bone screw is configured to rotate within the base member and further configured to be angled into the opening of the base member.

9. The multi-axial assembly of claim 1, wherein the crown engages a planar surface extending perpendicular to an axis defined by the receiver when the crown is received in the receiver.

10. The multi-axial assembly of claim 1, wherein the mating feature includes a plurality of surface projections extending from an outer surface of the crown, the projections being uniformly spaced apart and disposed circumferentially about the outer surface of the crown, the projections being disposed in indentations extending into an upper surface of the base member, the indentations being uniformly spaced apart and disposed circumferentially about the upper surface of the base member.

11. The multi-axial assembly of claim 1, wherein the mating feature includes a plurality of indentations extending into an outer surface of the crown, the indentations being uniformly spaced apart and disposed circumferentially about the outer surface of the crown, the indentations having projections extending from an upper surface of the base member disposed therein, the projections being uniformly spaced apart and extending circumferentially from the upper surface of the base member.

12. The multi-axial assembly of claim 1, wherein:
   an inner surface of the receiver that defines the distal portion comprises a first recess and an outer surface of the base member comprises a second recess; and
   the multi-axial assembly further comprising a snap ring positioned within the recesses to rotatably connect the base member with the receiver.

13. The multi-axial assembly of claim 1, further comprising the rod, wherein the rod engages the uppermost planar surface when the rod is positioned within the channel.

14. The multi-axial assembly of claim 1, wherein the base member has a maximum width that is greater than that of the aperture of the receiver such that the base member is configured to be bottom-loaded into the aperture of the receiver.

* * * * *

UNITED STATES PATENT AND TRADEMARK OFFICE
CERTIFICATE OF CORRECTION

| | | |
|---|---|---|
| PATENT NO. | : 9,232,969 B2 | Page 1 of 1 |
| APPLICATION NO. | : 12/915634 | |
| DATED | : January 12, 2016 | |
| INVENTOR(S) | : Farris | |

It is certified that error appears in the above-identified patent and that said Letters Patent is hereby corrected as shown below:

In the specification,

In Column 3, Line 49, delete "crown 32." and insert -- crown 33. --, therefor.

Signed and Sealed this
Twenty-third Day of August, 2016

Michelle K. Lee
*Director of the United States Patent and Trademark Office*